United States Patent
Tanriover et al.

(10) Patent No.: US 10,470,674 B2
(45) Date of Patent: Nov. 12, 2019

(54) TECHNOLOGIES FOR A FABRIC ACOUSTIC SENSOR

(71) Applicant: Intel Corporation, Santa Clara, CA (US)

(72) Inventors: Cagri Tanriover, Istanbul (TR); Cliodhna Ni Scanaill, Broadford (IE)

(73) Assignee: Intel Corporation, Santa Clara, CA (US)

( * ) Notice: Subject to any disclaimer, the term of this patent is extended or adjusted under 35 U.S.C. 154(b) by 726 days.

(21) Appl. No.: 15/073,003

(22) Filed: Mar. 17, 2016

(65) Prior Publication Data

US 2017/0265760 A1    Sep. 21, 2017

(51) Int. Cl.
*G01L 1/14*    (2006.01)
*A61B 5/024*    (2006.01)
(Continued)

(52) U.S. Cl.
CPC ......... *A61B 5/02444* (2013.01); *G01H 11/06* (2013.01); *G01L 1/165* (2013.01);
(Continued)

(58) Field of Classification Search
CPC ......... G01N 33/346; G01N 2203/0282; G01N 3/08; G01N 33/36; G01N 33/365; G01N 2203/0278; G01N 2203/0682; G01N 33/362; G01N 33/367; G01N 33/4833; G01N 3/20; G01N 15/0826; G01N 19/04; G01N 2021/8444; G01N 2033/0086; G01N 2203/0647; G01N 2291/2632; G01N 29/041; G01N 29/045; G01N 3/04;
(Continued)

(56) References Cited

U.S. PATENT DOCUMENTS 5,825,501 A * 10/1998 Mee .................. G01N 21/8983
356/429
7,398,690 B1    7/2008 Erickson et al.
(Continued)

FOREIGN PATENT DOCUMENTS

CA    2753535 A1 * 9/2010 ............... G01L 1/18
DE    102004025237 A1 * 3/2005 ............... G01L 1/20
(Continued)

OTHER PUBLICATIONS

MIT News, "Fibers that can hear and sing," http://news.mit.edu/2010/acoustic-fibers-0712, retrieved Feb. 8, 2016.
(Continued)

*Primary Examiner* — Andre J Allen
(74) *Attorney, Agent, or Firm* — Barnes & Thornburg LLP

(57) ABSTRACT

Technologies for a fabric acoustic sensor are disclosed. The fabric acoustic sensor includes a conductive thread and a non-conductive thread, which form a diaphragm that vibrates in response to a sound wave. As a result of the vibration, the conductive thread stretches, and a resistance of the conductive thread varies. The change in resistance is measured by a compute device, and the compute device may determine the sound wave based on the change in resistance. In some embodiments, the fabric acoustic sensor may be used to monitor a heart rate, locate an object, and/or provide an input for noise cancellation.

10 Claims, 4 Drawing Sheets

(51) Int. Cl.
*G01S 3/86* (2006.01)
*G01N 21/898* (2006.01)
*G01L 5/00* (2006.01)
*G01L 1/16* (2006.01)
*G01H 11/06* (2006.01)

(52) U.S. Cl.
CPC ............ *G01L 5/00* (2013.01); *G01N 21/8983* (2013.01); *G01S 3/86* (2013.01); *G10K 2210/3226* (2013.01)

(58) Field of Classification Search
CPC .......... G01N 3/12; G01N 3/307; G01N 3/313; G01N 3/317; G01N 15/08; G01N 19/02; G01N 21/1702; G01N 21/27; G01N 21/3559; G01N 21/64; G01N 21/80; G01N 21/84; G01N 21/8901; G01N 21/8914; G01N 21/8915; G01N 21/8983; G01N 21/91; G01N 2201/062; G01N 2203/0019; G01N 2203/0023; G01N 2203/0064; G01N 2203/0089; G01N 2203/0096; G01N 2203/021; G01N 2203/0216; G01N 2203/0222; G01N 2203/024; G01N 2203/0246; G01N 2203/0248; G01N 2203/0254; G01N 2203/0298; G01N 2203/0494; G01N 2223/01; G01N 2223/04; G01N 2223/076; G01N 2291/012; G01N 2291/015; G01N 2291/0231; G01N 2291/0232; G01N 2291/02827; G01N 2291/0289; G01N 2291/0422; G01N 2291/102; G01N 2291/106; G01N 22/00; G01N 29/04; G01N 29/07; G01N 29/11; G01N 29/12; G01N 29/14; G01N 29/223; G01N 29/2418; G01N 29/27; G01N 29/348; G01N 29/44; G01N 29/4427; G01N 29/4454; G01N 29/48; G01N 33/38; G01N 33/44; G01N 33/445; G01N 33/483; G01N 35/04; G01N 37/00; G01N 3/02; G01N 3/26; G01N 3/28; G01N 3/46; G01N 3/58; G01N 5/025; G01N 9/36; G01N 3/56; G01N 2291/02854; G01N 2291/014; G01N 2203/0003; G01N 2033/0083; G01N 2021/8917; G01N 2021/8663; G01N 1/286; G01N 2291/0237; G01N 2203/028; G01N 33/34; G01N 2203/0226; G01N 21/57; G01N 21/8803; G01N 2203/001; G01N 33/442; G01N 2203/0641; G01N 2203/027; G01N 2203/0232; G01N 2203/0048

USPC ........................................................ 73/159
See application file for complete search history.

(56) References Cited

U.S. PATENT DOCUMENTS

| 2007/0056377 | A1 | 3/2007 | Matsubara | |
| 2009/0140167 | A1* | 6/2009 | Ward | B82Y 15/00 250/458.1 |
| 2010/0077863 | A1 | 4/2010 | Miyoshi et al. | |
| 2011/0094306 | A1* | 4/2011 | Bratkovski | B25J 13/084 73/849 |
| 2015/0104048 | A1 | 4/2015 | Uchida et al. | |
| 2016/0018274 | A1* | 1/2016 | Seitz | G01D 5/2417 73/862.626 |
| 2017/0038322 | A1* | 2/2017 | Cobanoglu | D03D 1/0088 |
| 2018/0302983 | A1* | 10/2018 | Osorio Dinis | H03K 17/9622 |

FOREIGN PATENT DOCUMENTS

| EP | 1300504 A1 * | 4/2003 | ............... D06H 3/08 |
| JP | 2014-529266 | 10/2014 | |
| WO | WO-2016149847 A1 * | 9/2016 | ........... B65H 63/064 |

OTHER PUBLICATIONS

Berglin and Zetterblom, "Textile Sound Structures," Ambience'08, Borås, Sweden.
Google Project Jacquard, https://www.google.com/atap/project-jacquard, retrieved Feb. 8, 2016.
Sensoria Smart Socks, http://www.sensoriafitness.com/Technology, retrieved Feb. 8, 2016.
Visijax Commuter Jacket, https://www.visijax.com/products/led-jackets-and-gilets/the-commuter-jacket/, retrieved Feb. 8, 2016.
BAE systems wearable antenna, http://www.baesystems.com/cs/Satellite?c=BAEMedia_C&childpagename=Global%2FBAELayout&cid=1434554934221&pagename=GlobalWrapper, retrieved Feb. 8, 2016.
Soldiers body uniform, http://www.cnet.com/news/wearables-at-war-how-smart-textiles-are-lightening-the-load-for-soldiers, retrieved Feb. 8, 2016.
Castano and Flatau, "Smart fabric sensors and e-textile technology: a review," Smart Materials and Structures, 23, 053001 (2014).
"Stretchy battery woven into fabric," Nature 510, 314 (2014) (Article preview).
Egusa et al., "Multimaterial piezoelectric fibers," Nat. Materials 9, 643 (2010).
Ren et al., "Elastic and Wearable Wire-Shaped Lithium-Ion Battery with High Electrochemical Performance", Angewandte Chemie, 126, 7998 (2014) (Abstract).
International search report for PCT application No. PCT/US2017/017883, dated May 19, 2017 (3 pages).
Written opinion for PCT application No. PCT/US2017/017883, dated May 19, 2017 (4 pages).

* cited by examiner

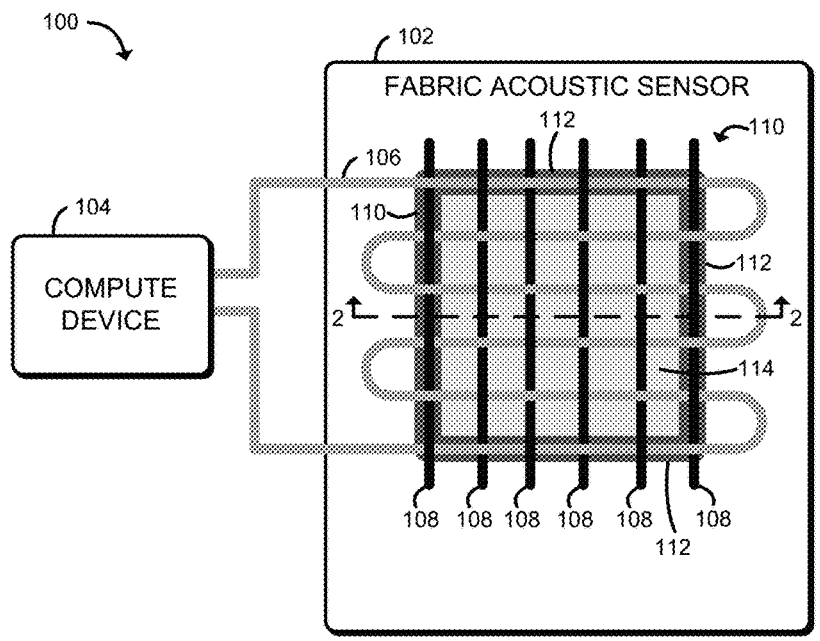
FIG. 1
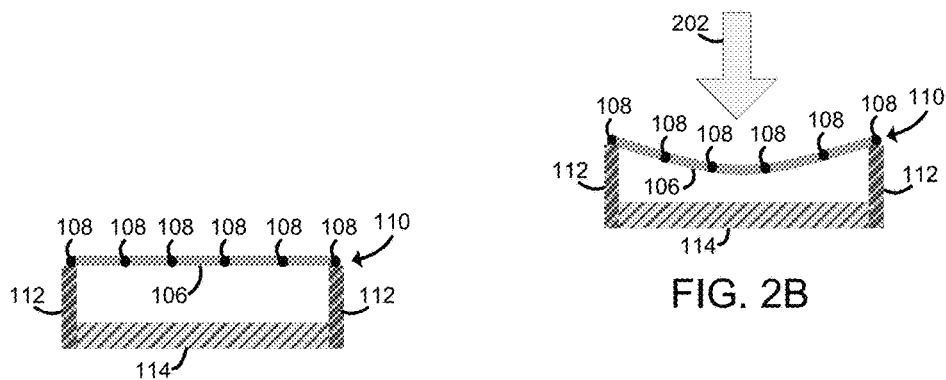
FIG. 2A
FIG. 2B
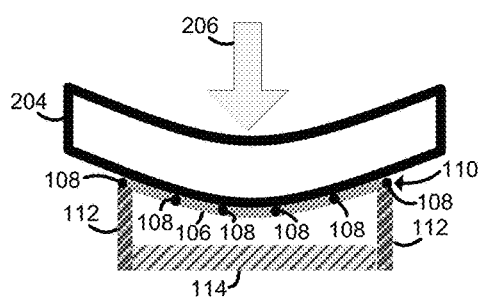
FIG. 2C

TECHNOLOGIES FOR A FABRIC ACOUSTIC SENSOR

BACKGROUND

Rapid advances in sensor technology are enabling the move from standalone sensor modules to wearable electronics to disappearable electronics that are integrated into aspects of our lives not typically associated with electronics. Disappearable electronics include those electronics that have become so integrated into a user and/or accoutrements of the user as to be nearly indistinguishable, such as sensor tattoos on the skin, sensor earbuds, ingestible electronics, and sensors integrated into fabrics. For example, electronic fabrics can include circuits, sensors, actuators, batteries, energy generators, and antennas.

Electronics integrated into fabrics offer a number of advantages over traditional electronics in certain circumstances. Integration of a sensor into a fabric during manufacture allows for the sensor to be any size or shape. Additionally, sensors can be integrated in ways traditional sensors cannot, due to the size, shape, or weight of the traditional sensor.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

FIG. 1 is a simplified diagram of at least one embodiment of a system for fabric-based acoustic sensing;

FIGS. 2A-2C are simplified diagrams of at least one embodiment of a fabric acoustic sensor of the system for fabric-based acoustic sensing of FIG. 1;

DETAILED DESCRIPTION OF THE DRAWINGS

Figure 3:
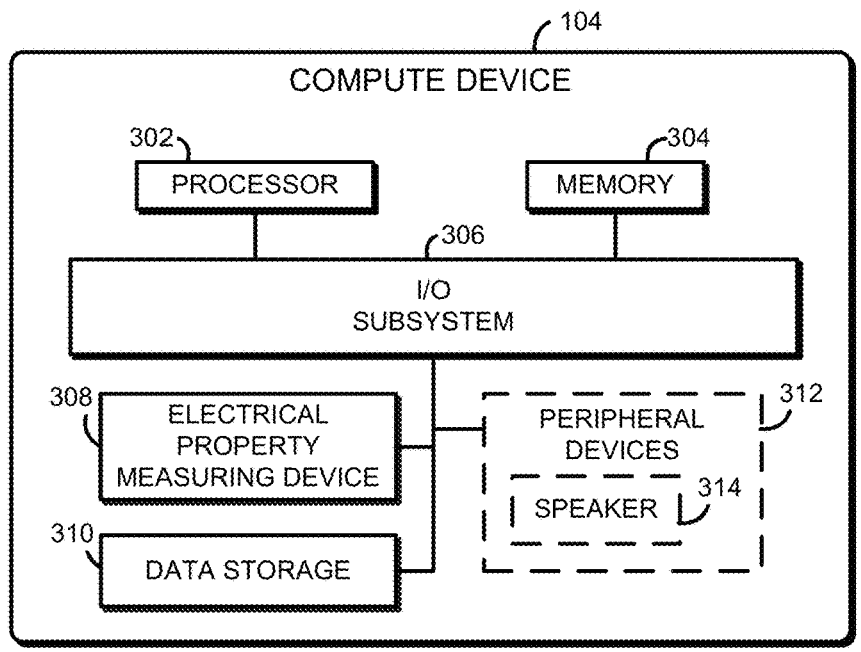
FIG. 3 is a simplified block diagram of at least one embodiment of a compute device of the system for fabric-based acoustic sensing of FIG. 1.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C): (A and B); (B and C); (A and C); or (A, B, and C). Similarly, items listed in the form of "at least one of A, B, or C" can mean (A); (B); (C): (A and B); (B and C); (A and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, an illustrative system 100 for fabric-based acoustic sensing includes a fabric acoustic sensor 102 and a compute device 104. The illustrative fabric acoustic sensor 102, described in more detail below, includes a conductive thread 106 interwoven (or knitted) with one or more non-conductive threads 108 to form a diaphragm 110 The conductive thread 106 has an associated resistance which changes when the conductive thread 106 is stretched. It should be appreciated that, throughout this disclosure, "conductive" refers to electrically conductive (as opposed to, e.g., thermally conductive). In the illustrative embodiment, the fabric acoustic sensor 102 includes four side chamber walls 112 and a back chamber wall 114. In use, as described in more detail below, a sound wave causes the diaphragm 110 formed by the conductive thread 106 and the non-conductive threads 108 to vibrate. As used herein, a sound wave includes any pressure wave in a liquid, gas, or solid, including vibrations. The vibration from the sound wave causes the conductive thread 106 to stretch and relax, which causes the associated resistance to change as well. The compute device 104 is connected to the conductive thread 106, and is configured to measure this change in the associated resistance. From the measured change in resistance, the compute device 104 is able to determine data indicative of the sound wave that caused the vibration. In some embodiments, the conductive thread 106 is connected directly to the compute device 104. In other embodiments, there may be an intermediate connection connecting the conductive thread 106 to the compute device 104, such as a wire having a lower resistance per unit length than the conductive thread 106. In the illustrative embodiment, the compute device 104 is connected to the two ends of the conductive thread 106. In other embodiments, one or both of the connections from the compute device 104 to the conductive thread 106 may be in the middle of the conductive thread 106 or otherwise not at the end of the conductive thread 106.

The fabric acoustic sensor 102 may be integrated into any number of common items, such as clothing, upholstery (on a chair, couch, etc.), bedding, tarps, etc., for a variety of possible uses. In some embodiments, the fabric acoustic sensor 102 may include an array of diaphragms, possibly of different shapes or sizes, which may be used together. The array of diaphragms 110 may be arranged in a 2-dimensional pattern, such as in a grid with regularly-placed diaphragms 110 (e.g., one diaphragm 110 at each intersection of the grid lines). Each diaphragm 110 of the array of diaphragms 110 may be the same embodiment of a diaphragm 110 or may be a different embodiment of a diaphragm 110 (the various embodiments of a diaphragm 110 are described in more detail below, e.g. in FIGS. 6A-6F). For example, some of the diaphragms 110 of the array may have chambers behind them, while other diaphragms of the array may be secured to anchoring objects that do not form chambers. Each diaphragm 110 of the array may have its own conductive thread 106, or one or more of the diaphragms 110 may include different portions of the same conductive thread 106. Of course, in embodiments in which one conductive thread 106 is included in different diaphragms 110, different electrical properties of the conductive thread 106 may be measured for each diaphragm 110, such as the resistance of the portion of the conductive thread 106 corresponding to that diaphragm 110. Additionally, some embodiments may include an array of fabric acoustic sensors 102, which may be different shapes or sizes, and may be used together and arranged in a similar manner as the array of diaphragms 110 described above, and may perform similar functions as an array of diaphragms 110 described below.

A fabric acoustic sensor 102 with one or more diaphragms 110 may be used for various applications. For example, a fabric acoustic sensor 102 could be used to continuously monitor vital signs with an auditory signature, such as blood pressure or heart rate. Additionally or alternatively, a fabric acoustic sensor 102 with a diaphragm 110 or an array of diaphragms 110 could be used for object location or indoor navigation by using echo location, triangulation, or trilateration. In some embodiments, a fabric acoustic sensor 102 with a diaphragm 110 or an array of diaphragms 110 could be used in an environment such as an office environment where cancellation of ambient noise is desired. Additionally, in some embodiments, after the fabric acoustic sensor 102 measures a sound, a speaker 314 could be used to cancel out the sound. Of course, in some embodiments, the fabric acoustic sensor 102 could be used as a generic microphone for capturing sound, such as human voices, environmental noises, music, etc.

The conductive thread 106 may be embodied as any type of continuous conductive thread that has a resistance that changes when the thread is stretched and that can be integrated into a fabric. For example, the conductive thread 106 may be a flexible substrate with a conductive coating. The flexible substrate may include polyester, nylon, cotton, silk, flax fiber (i.e., linen), wool, etc. In additional embodiments, the conductive thread 106 may be formed from a conductive rubber, or may be embodied as a thread with flexible graphene embedded in the fibers. The non-conductive thread 108 may be any type of non-conductive thread amenable to being woven with the conductive thread 108, such as polyester, nylon, cotton, silk, flax fiber, wool, etc. In the illustrative embodiment, the conductive thread 106 follows a meandering course, crossing the diaphragm 110 several times, as shown in FIG. 1. In other embodiments, the conductive thread 106 may cross the diaphragm 110 only once, or may not even fully cross any part of the diaphragm 110. In the illustrative embodiment, no point of the conductive thread 106 touches another point of the conductive thread 106 (i.e., the conductive thread 106 does not cross itself). This configuration ensures that the resistance measured across the two ends of the conductive thread 106 does not change due to the presence of additional paths for current through the conductive thread 106. In additional embodiments, the compute device 104 may be capable of using the fabric acoustic sensor 102 even if conductive thread 106 crosses itself and one point of the conductive thread 106 touches another point of the conductive thread 106.

The side chamber walls 112 and the back chamber wall 114 may be formed from any material suitable for securing the diaphragm 110 formed by the conductive thread 106 and the non-conductive thread 108. In some embodiments, the side chamber walls 112 and/or the back chamber wall 114 may be a rigid or inflexible material that can hold the diaphragm 110 in place without warping, such as a rigid foam. In other embodiments, the side chamber walls 112 and/or the back chamber wall 114 may be a flexible material. The conductive thread 106 and/or the non-conductive thread 108 may be secured to the side chamber walls 112 using any securing means, such as glue, additional threads, hooks, etc.

Referring now to FIG. 2A, an illustrative embodiment of the fabric acoustic sensor 102 is shown in cross-section. When the diaphragm 110 formed by the conductive thread 106 and the non-conductive threads 108 is in the resting position (e.g., when no vibration is present), in the illustrative embodiment, the side chamber walls 112 hold the diaphragm 110 taut. In additional embodiments, the diaphragm 110 may be slack.

Referring now to FIG. 2B, an illustrative embodiment of the fabric acoustic sensor 102 is shown in cross-section when a vibration is present. A sound wave in air or other fluid, represented by the arrow 202, pushes on the diaphragm 110 formed by the conductive thread 106 and the non-conductive thread 108. The diaphragm 110 is deflected into the chamber formed by the side chamber walls 112 and the back chamber wall 114 in response to the sound wave. The deflection stretches the conductive thread 106, and changes the associated resistance.

Referring now to FIG. 2C, an additional embodiment of the fabric acoustic sensor 102 is shown in cross-section in which the fabric acoustic sensor 102 is mechanically coupled to a solid material 204. A sound wave in the solid material 204, represented by the arrow 206, is transmitted through the mechanical coupling and causes the diaphragm 110 to be deflected into the chamber formed by the side chamber walls 112 and the back chamber wall 114. It should be appreciated that the sound wave in the solid material 204 may be a longitudinal wave or a transverse wave.

Referring now to FIG. 3, the compute device 104 may be embodied as any type of compute device capable of performing the functions described herein. For example, the compute device 104 may be embodied as or otherwise be included in, without limitation, a wearable computer, an embedded computing system, a System-on-a-Chip (SoC), a smartphone, a cellular phone, a tablet computer, a notebook computer, a laptop computer, a handset, a messaging device, a camera device, a desktop computer, a server computer, a multiprocessor system, a processor-based system, a consumer electronic device, and/or any other compute device.

The illustrative compute device 104 includes a processor 302, a memory 304, an input/output (I/O) subsystem 306, an electrical property measuring device 308, and data storage 310. In some embodiments, one or more of the illustrative components of the compute device 104 may be incorporated in, or otherwise form a portion of, another component. For example, the memory 304, or portions thereof, may be incorporated in the processor 302 in some embodiments.

The processor 302 may be embodied as any type of processor capable of performing the functions described herein. For example, the processor 302 may be embodied as a single or multi-core processor(s), a single or multi-socket processor, a digital signal processor, a microcontroller, a field programmable gate array (FPGA), or other processor or processing/controlling circuit. Similarly, the memory 304 may be embodied as any type of volatile, non-volatile, or hybrid (i.e., containing both volatile and non-volatile components) memory or data storage capable of performing the functions described herein. In operation, the memory 304 may store various data and software used during operation of the compute device 104 such as operating systems, applications, programs, libraries, and drivers. The memory 304 is communicatively coupled to the processor 302 via the I/O subsystem 306, which may be embodied as circuitry and/or components to facilitate input/output operations with the processor 302, the memory 304, and other components of the compute device 104. For example, the I/O subsystem 306 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 306 may form a portion of a system-on-a-chip (SoC) and be incorporated, along with the processor 302, the memory 304, and other components of the compute device 104 on a single integrated circuit chip.

The electrical property measuring device 308 may be embodied as any type of device capable of measuring an electrical property of the conductive thread 106. For example, the electrical property measuring device 308 may be embodied as an ohmmeter to measure the resistance of the conductive thread 106. In some embodiments, the ohmmeter may employ a constant current source that passes a known current through the conductive thread 106 and measure the voltage drop across the conductive thread 106. In other embodiments, the ohmmeter may employ a voltage divider with a constant voltage and a resistor of know resistance in series with the conductive thread 106 and measure the voltage at the junction of the resistor and the conductive thread 106. In additional embodiments, the ohmmeter may employ a difference measurement such that the measurement is essentially zero when the conductive thread 106 is not deflected due to a sound wave, and the measurement is non-zero when the conductive thread 106 is deflected due to a sound wave. For example, the ohmmeter may employ a Wheatstone bridge, a Kelvin bridge, etc. In such embodiments, the electrical property measuring device 308 may include a device capable of measuring small currents or voltages, such as a picoammeter. Of course, in some embodiments, the electrical property measuring device 308 may measure an electrical property of the conductive thread 106 indicative of a resistance of the conductive thread 106 without directly measuring the resistance of the conductive thread 106.

The data storage 310 may be embodied as any type of device or devices configured for the short-term or long-term storage of data. For example, the data storage 310 may include any one or more memory devices and circuits, memory cards, hard disk drives, solid-state drives, or other non-volatile data storage devices.

Of course, in some embodiments, the compute device 104 may include other or additional components, such as those commonly found in a compute device. For example, the compute device 104 may also have peripheral devices 312 such as a speaker 314, display, keyboard, mouse, camera, communication circuit, etc.

Figure 4:
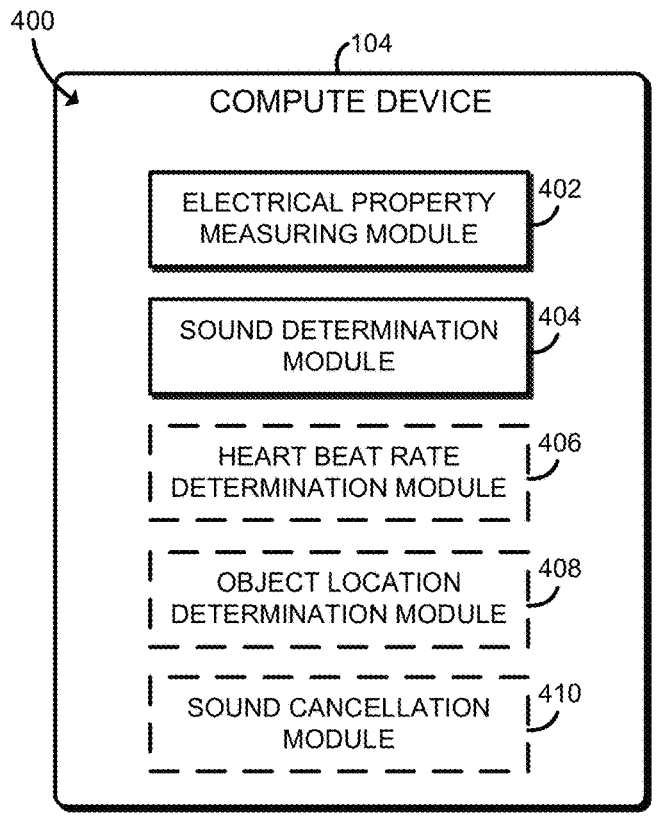
FIG. 4 is a block diagram of at least one embodiment of an environment that may be established by the compute device of FIG. 3.

Referring now to FIG. 4, in use, the compute device 104 may establish an environment 400. The illustrative environment 400 includes an electrical property measuring module 402 and a sound determination module 404. The various modules of the environment 400 may be embodied as hardware, software, firmware, or a combination thereof. For example, the various modules, logic, and other components of the environment 400 may form a portion of, or otherwise be established by, the processor 302 or other hardware components of the compute device 104, such as the memory 304. As such, in some embodiments, one or more of the modules of the environment 400 may be embodied as circuitry or collection of electrical devices (e.g., an electrical property measuring circuit 402 and/or a sound determination circuit 404). It should be appreciated that, in such embodiments, one or more of the circuits (e.g., the electrical property measuring circuit 402 and/or the sound determination circuit 404) may form a portion of one or more of the processor 302, the memory 304, the I/O subsystem 306, the electrical property measuring device 308, and/or the data storage 310. Additionally, in some embodiments, one or more of the illustrative modules may form a portion of another module and/or one or more of the illustrative modules may be independent of one another.

The electrical property measuring module 402 is configured to measure an electrical property of the conductive thread 106. The electrical property measuring module 402 may measure the electrical property of the conductive thread 106 continuously, continually, and/or when so directed by the compute device 104, such as in response to a user command. The electrical property measuring module 402 may measure the electrical property of the conductive thread 106 every 20 microseconds, every 100 microseconds, every 20 milliseconds, or some other amount higher or lower than those amounts.

The sound determination module 404 is configured to determine data indicative of a sound wave causing the conductive thread 106 to vibrate based on the electrical property measured by the electrical property measuring module 402. For example, in some embodiments, the change in resistance from the resting position may vary as the square of the instantaneous deflection, and the sound determination module 404 may determine a pressure of the sound wave as a function of time by taking the square root of the difference between a measured resistance when the diaphragm 110 is in the resting position and another measured resistance when the diaphragm 110 is deflected due to a vibration.

In some embodiments, the compute device 104 may include additional modules configured to perform particular functions based on the sound determined by the sound determination module 404 and/or the electrical property measured by the electrical property measuring module 402. For example, in some embodiments, the compute device 104 may include a heart beat rate determination module 406, an object location determination module 408, and/or a sound cancellation module 410. In embodiments in which the fabric acoustic sensor 102 may be mechanically coupled to a human or animal body (e.g., by the fabric acoustic sensor 102 being embedded in an article of clothing), the heart beat rate determination module 406 is configured to determine a rate of a heart beat based on the determined sound.

The object location determination module 408 is configured to determine the location of an object based on the determined sound, e.g. by using echo location, triangulation, or trilateration. In some embodiments, the objects being located may include walls, which may be useful for indoor navigation.

The sound cancellation module 410 is configured to use the speaker 314 to cancel a determined sound. For example, the speaker 314 may generate a sound wave that destructively interferes partially or completely with the determined sound.

Figure 5:
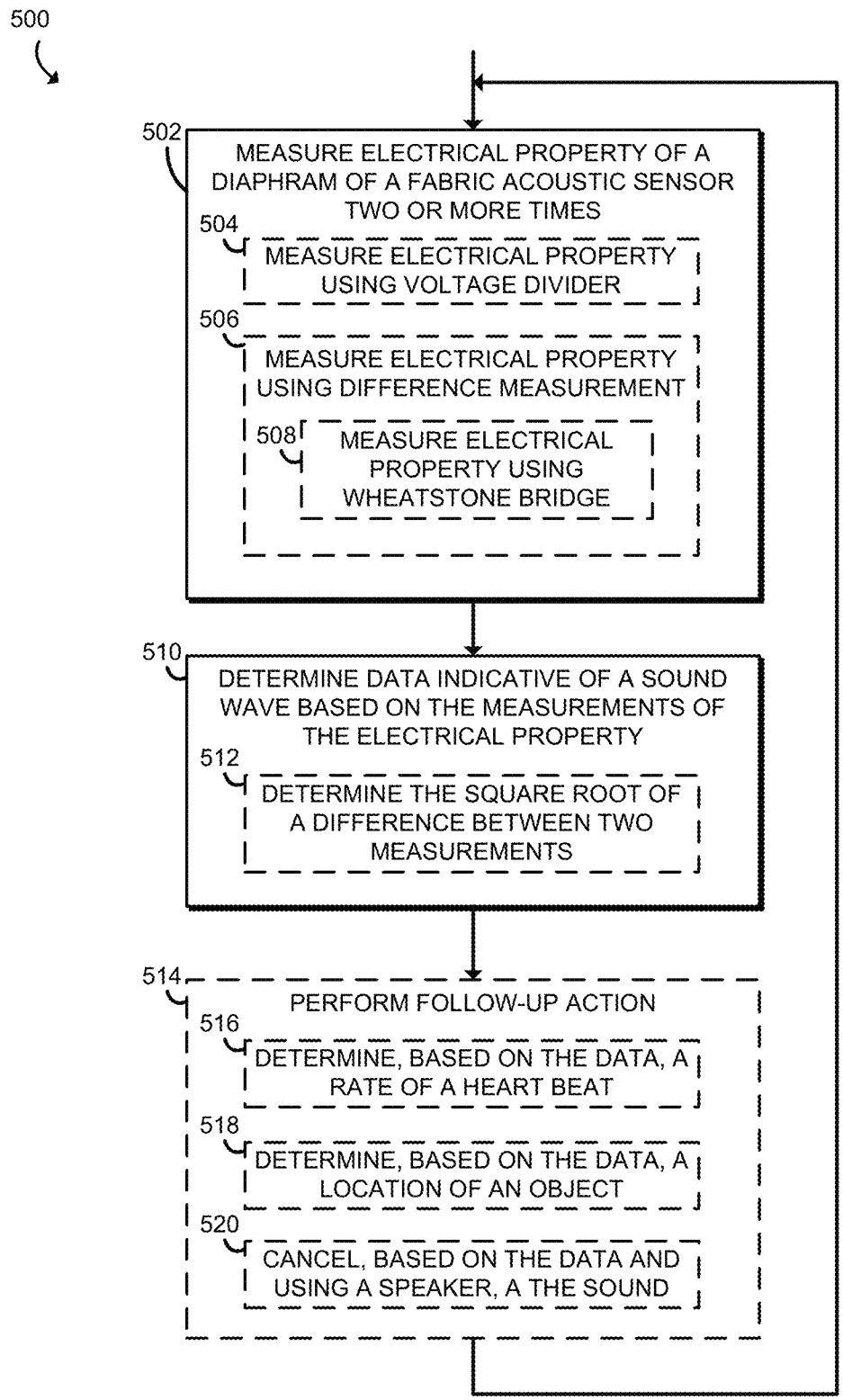
FIG. 5 is a simplified flow diagram of at least one embodiment of a method for detecting sound using a fabric acoustic sensor that may be executed by the compute device of FIG. 3.

Referring now to FIG. 5, in use, the compute device 104 may execute a method 500 for detecting a sound with a fabric acoustic sensor 102. The method 500 begins with block 502 in which the compute device 104 measures an electrical property of a diaphragm 110 of a fabric acoustic sensor 102 two or more times. As described in more detail above, the electrical property is dependent on a resistance of a conductive thread 106 of the diaphragm 110 and is variable based on a vibration of the diaphragm 110 in response to the sound. At least one of the measurements may be taken when the conductive thread 106 is not deflected from its resting position. In some embodiments, the compute device 104 may measure the electrical property of the diaphragm 110 using a voltage divider in block 504. In other embodiments, the compute device 104 may measure the electrical property of the diaphragm 110 using a difference measurement in block 506. For example, the compute device 104 may use a Wheatstone in block 508. In some embodiments, such as with an array of diaphragms 110 (or an array of fabric acoustic sensors 102), the compute device 104 may measure an electrical property of each diaphragm 110 of the array of diaphragms 110 (or of each fabric acoustic sensor 102 of the array of fabric acoustic sensors 102) two or more times.

In block 510, the compute device 104 determines data indicative of a sound wave based on the measurements of the electrical property. In an embodiment, the compute device 104 may determine the square root of a difference between two measurements of the electrical property of the conductive thread 106 in block 512.

In some embodiments, the compute device 104 may perform a follow-up action based on the data indicative of the sound wave in block 514. For example, in an embodiment where the fabric acoustic sensor 102 is mechanically coupled to a human or animal body (e.g., by an article of clothing in which the fabric acoustic sensor 102 is embedded), the compute device 104 may determine a rate of a heart beat based on the data in block 516. In another example, the compute device 104 determines the location of an object in block 518, e.g. by using echo location, triangulation, or trilateration. In this example, the compute device 104 may use data from an array of diaphragms 110 (or from an array of fabric acoustic sensors 102). In a third example, the compute device 104 uses a speaker 314 to cancel the sound in block 520. In this example, the compute device 104 may use data from an array of diaphragms 110 (or from an array of fabric acoustic sensors 102). Of course, in some embodiments, the fabric acoustic sensor 102 may be used as a generic microphone for capturing sound, such as human voices, environmental noises, music, etc. The method 500 then returns to block 502.

Referring now to FIGS. 6A-6F, various additional embodiments of the fabric acoustic sensor 102 are shown. Note that the additional embodiments shown are merely a sample of the possible embodiments, and FIG. 2A and FIGS. 6A-6F are not an exhaustive list of every possible embodiment. It should be appreciated that some or all of the embodiments shown may be combined with other embodiments. For example, FIG. 6B may include the back chamber wall 114 shown in FIG. 2A.

Figure 6A:
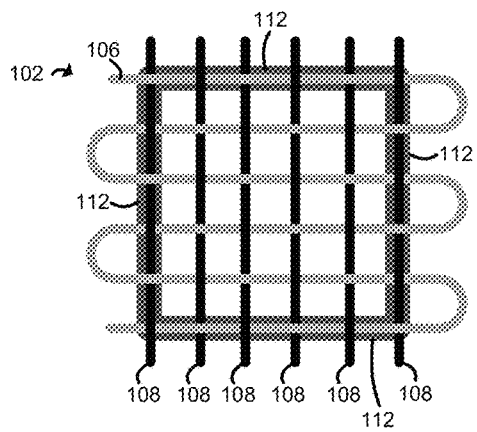
FIGS. 6A-6F are simplified diagrams of additional embodiments of the fabric acoustic sensor of the system for fabric-based acoustic sensing of FIG. 1.

Referring now to FIG. 6A, in some embodiments, the fabric acoustic sensor 102 may include the four side chamber walls 112 (without the back chamber wall 114 of FIG. 2A). Of course, in such an embodiment, the chamber walls may not actually form a chamber. In similar embodiments, there may be a different number of side chamber walls 112 and/or the side chamber walls 112 may be curved. For example, may be three side chamber walls 112 forming a triangle, or there may be one side chamber wall 112 curved into a loop (e.g., a circle).

Figure 6B:
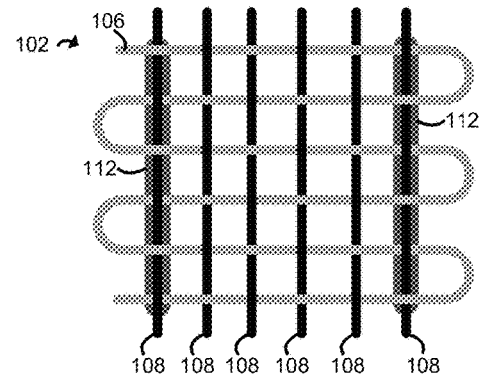
Figure 6C:
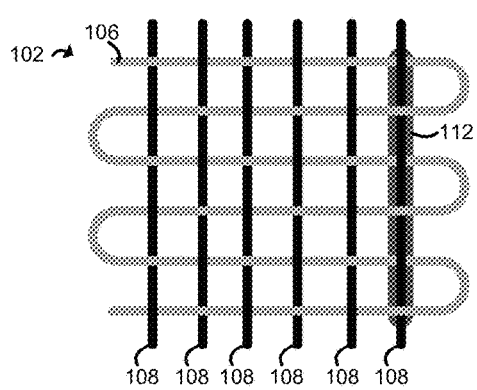

Referring now to FIG. 6B, in some embodiments, the fabric acoustic sensor 102 may include two or more side chamber walls 112 that establish a diaphragm 110 of the fabric between them, but without fully encircling the diaphragm 110. In an additional embodiment in FIG. 6C, the fabric acoustic sensor 102 may include only a single side chamber wall 112, which may be straight or curved.

Figure 6D:
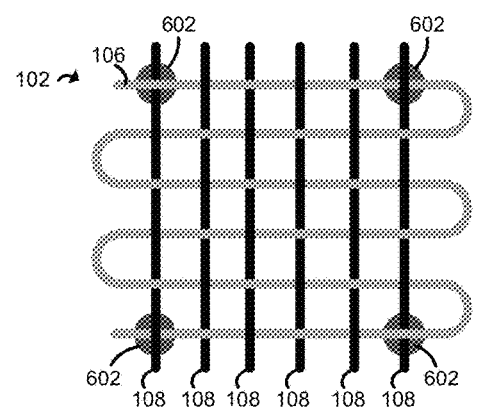
Figure 6E:
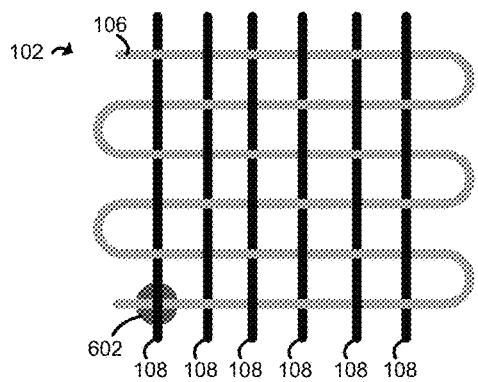
Figure 6F:
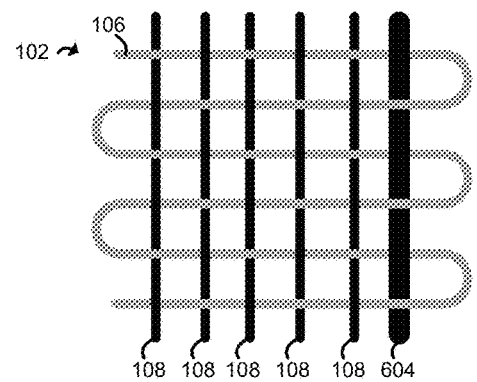

Referring now to FIG. 6D, in some embodiments, the fabric acoustic sensor 102 may include anchoring objects 602 secured to the conductive thread 106 and/or the non-conductive threads 108. Additionally, in some embodiments, the fabric acoustic sensor 102 may only include a single anchoring object 602, as shown in FIG. 6E. In some embodiments, a region of the fabric acoustic sensor 102 may be secured by the presence of a heavy thread 604 that may vibrate less in response to a sound wave than the other threads in the fabric acoustic sensor 102, as shown in FIG. 6F.

It should be appreciated that, despite not completely encircling a diaphragm 110 of the fabric as in FIG. 6A, FIGS. 6B-6F and similar embodiments can still be used as a fabric acoustic sensor. For example, each of those embodiments include a first region including at least part of the fabric that is not secured and a second region including at least part of the fabric that is secured to an object (e.g., secured to a side chamber wall 112). When a sound wave impacts the fabric acoustic sensor 102, the first region and second region each vibrate in response with a certain amplitude. Of course, since the second region is secured to the object, the second region will vibrate with the same amplitude as that object. If the object responds less to a vibration (e.g., if the object is denser or heavier than the fabric, or otherwise less susceptible to being moved by a sound wave), then the second region will also respond less. Thus, the second region will vibrate with a smaller amplitude than the first region, and therefore the conductive thread 106 spanning the two regions will be stretched in response.

EXAMPLES

Illustrative examples of the devices, systems, and methods disclosed herein are provided below. An embodiment of the devices, systems, and methods may include any one or more, and any combination of, the examples described below.

Example 1 includes a fabric acoustic sensor comprising a diaphragm comprising a conductive thread interwoven with a non-conductive thread; and a chamber wall coupled to the diaphragm to form a chamber, wherein the diaphragm is to deflect into the chamber in response to a sound wave and the conductive thread has a resistance that is variable based on the deflection of the diaphragm.

Example 2 includes the subject matter of Example 1, and wherein the conductive thread comprises a flexible substrate with a conductive coating.

Example 3 includes the subject matter of any of Examples 1 and 2, and wherein the flexible substrate comprises polyester.

Example 4 includes the subject matter of any of Examples 1-3, and wherein the flexible substrate comprises nylon.

Example 5 includes the subject matter of any of Examples 1-4, and wherein the conductive thread comprises a conductive rubber fiber.

Example 6 includes the subject matter of any of Examples 1-5, and wherein the chamber is an inner chamber, and wherein the chamber wall is located behind the diaphragm and comprises four side chamber walls and a back chamber wall.

Example 7 includes the subject matter of any of Examples 1-6, and, wherein the chamber wall comprises four side chamber walls and a back chamber wall.

Example 8 includes the subject matter of any of Examples 1-7, and wherein the chamber wall comprises rigid foam.

Example 9 includes the subject matter of any of Examples 1-8, and wherein the chamber wall secures the diaphragm such that the diaphragm is taut.

Example 10 includes the subject matter of any of Examples 1-9, and further including one or more additional diaphragms.

Example 11 includes the subject matter of any of Examples 1-10, and wherein the diaphragm and the one or more additional diaphragms are arranged in a grid and are regularly-placed.

Example 12 includes a method for detecting a sound with a fabric acoustic sensor, the method comprising measuring, by a compute device, an electrical property of a diaphragm of the fabric acoustic sensor at a first time to generate a first data point, wherein the electrical property is dependent on a resistance of a conductive thread of the diaphragm and the resistance is variable based on a vibration of the diaphragm in response to the sound; measuring, by the compute device, the electrical property at a second time to generate a second data point; and determining, by the compute device and based on the first data point and the second data point, data indicative of the sound.

Example 13 includes the subject matter of Example 12, and wherein measuring the electrical property of the diaphragm comprises measuring the resistance of the conductive thread.

Example 14 includes the subject matter of any of Examples 12 and 13, and wherein measuring the electrical property of the diaphragm comprises measuring the electrical property of the diaphragm with a voltage divider.

Example 15 includes the subject matter of any of Examples 12-14, and wherein measuring the electrical property of the diaphragm comprises measuring the electrical property of the diaphragm with a difference measurement device.

Example 16 includes the subject matter of any of Examples 12-15, and wherein the difference measurement device comprises a Wheatstone bridge.

Example 17 includes the subject matter of any of Examples 12-16, and wherein the diaphragm is mechanically coupled to a solid material, wherein the vibration of the diaphragm is caused by a vibration of the solid material.

Example 18 includes the subject matter of any of Examples 12-17, and wherein the diaphragm is mechanically coupled to a human body, wherein the sound comprises a heart beat, further comprising determining, by the compute device and based on the data, a rate of the heart beat.

Example 19 includes the subject matter of any of Examples 12-18, and further including determining, by the compute device and based on the data, a location of an object.

Example 20 includes the subject matter of any of Examples 12-19, and further including measuring, by the compute device, one or more additional electrical properties of one or more additional diaphragms of the fabric acoustic sensor at the first time to generate additional first data points, wherein each additional electrical property is dependent on a corresponding resistance of a conductive thread of the corresponding additional diaphragm and the corresponding resistance is variable based on a vibration of the corresponding additional diaphragm in response to the sound; measuring, by the compute device, the one or more electrical properties at the second time to generate additional second data points; determining, by the compute device and based on the first additional data points and the second additional data points, additional data indicative of the sound.

Example 21 includes the subject matter of any of Examples 12-20, and further including determining, by the compute device and based on the data and the additional data, a location of an object.

Example 22 includes the subject matter of any of Examples 12-21, and further including canceling the sound by a speaker of the compute device based on the data.

Example 23 includes a woven fabric comprising a conductive thread; one or more non-conductive threads interwoven with the conductive thread to form a fabric acoustic sensor of the woven fabric, wherein the fabric acoustic sensor comprises a first region and a second region and wherein the first region vibrates with a first amplitude in response to a sound wave and the second region vibrates with a second amplitude in response to the sound wave, and wherein the second region is secured such that the first amplitude is greater than the second amplitude.

Example 24 includes the subject matter of Example 23, and wherein the second region is secured to a chamber wall coupled to the fabric acoustic sensor and located behind the fabric acoustic sensor to form an inner chamber.

Example 25 includes the subject matter of any of Examples 23 and 24, and wherein the second region is secured to a rigid foam.

Example 26 includes the subject matter of any of Examples 23-25, and wherein the second region is secured to an anchoring object, wherein the anchoring object forms a loop such that the second region secured to the anchoring object encloses the first region.

Example 27 includes the subject matter of any of Examples 23-26, and wherein the second region is secured to an anchoring object, wherein the anchoring object comprises one or more chamber walls.

Example 28 includes the subject matter of any of Examples 23-27, and wherein the second region comprises a heavy thread, wherein the heavy thread is heavier than the non-conductive thread and the conductive thread, such that the heavy thread causes the second region to vibrate with the second amplitude smaller than the first amplitude in response to the sound wave.

Example 29 includes the subject matter of any of Examples 23-28, and wherein the second region is secured such that the first region is taut.

Example 30 includes the subject matter of any of Examples 23-29, and wherein the conductive thread comprises a flexible substrate with a conductive coating.

Example 31 includes the subject matter of any of Examples 23-30, and wherein the flexible substrate comprises polyester.

Example 32 includes the subject matter of any of Examples 23-31, and wherein the flexible substrate comprises nylon.

Example 33 includes the subject matter of any of Examples 23-32, and wherein the conductive thread comprises a conductive rubber fiber.

Example 34 includes the subject matter of any of Examples 23-33, and wherein the conductive thread comprises graphene embedded in a flexible substrate.

Example 35 includes a fabric acoustic sensor comprising means for measuring an electrical property of a diaphragm of the fabric acoustic sensor at a first time to generate a first data point, wherein the electrical property is dependent on a resistance of a conductive thread of the diaphragm and the resistance is variable based on a vibration of the diaphragm in response to a sound; means for measuring the electrical property at a second time to generate a second data point; and means for determining, based on the first data point and the second data point, data indicative of the sound.

Example 36 includes the subject matter of Example 35, and wherein the means for measuring the electrical property of the diaphragm comprises means for measuring the resistance of the conductive thread.

Example 37 includes the subject matter of any of Examples 35 and 36, and wherein the means for measuring the electrical property of the diaphragm comprises means for measuring the electrical property of the diaphragm with a voltage divider.

Example 38 includes the subject matter of any of Examples 35-37, and wherein the means for measuring the electrical property of the diaphragm comprises means for measuring the electrical property of the diaphragm with a difference measurement device.

Example 39 includes the subject matter of any of Examples 35-38, and wherein the difference measurement device comprises a Wheatstone bridge.

Example 40 includes the subject matter of any of Examples 35-39, and wherein the diaphragm is mechanically coupled to a solid material, wherein the vibration of the diaphragm is caused by a vibration of the solid material.

Example 41 includes the subject matter of any of Examples 35-40, and wherein the diaphragm is mechanically coupled to a human body, wherein the sound comprises a heart beat, further comprising means for determining, based on the data, a rate of the heart beat.

Example 42 includes the subject matter of any of Examples 35-41, and further including means for determining, based on the data, a location of an object.

Example 43 includes the subject matter of any of Examples 35-42, and further including means for measuring one or more additional electrical properties of one or more additional diaphragms of the fabric acoustic sensor at the first time to generate additional first data points, wherein each additional electrical property is dependent on a corresponding resistance of a conductive thread of the corresponding additional diaphragm and the corresponding resistance is variable based on a vibration of the corresponding additional diaphragm in response to the sound; means for measuring the one or more electrical properties at the second time to generate additional second data points; means for determining, based on the first additional data points and the second additional data points, additional data indicative of the sound.

Example 44 includes the subject matter of any of Examples 35-43, and further including means for determining, based on the data and the additional data, a location of an object.

Example 45 includes the subject matter of any of Examples 35-44, and further including means for canceling the sound based on the data.

The invention claimed is:

1. A fabric acoustic sensor comprising:
    a diaphragm comprising a conductive thread interwoven with a non-conductive thread; and
    a chamber wall coupled to the diaphragm to form a chamber,
    wherein the diaphragm is to deflect into the chamber in response to a sound wave and the conductive thread has a resistance that is variable based on the deflection of the diaphragm.

2. The fabric acoustic sensor of claim 1, wherein the conductive thread comprises a flexible substrate with a conductive coating.

3. The fabric acoustic sensor of claim 2, wherein the flexible substrate comprises polyester.

4. The fabric acoustic sensor of claim 1, wherein the conductive thread comprises a conductive rubber fiber.

5. The fabric acoustic sensor of claim 1, wherein the conductive thread comprises graphene embedded in a flexible substrate.

6. The fabric acoustic sensor of claim 1, wherein the chamber is an inner chamber, and wherein the chamber wall is located behind the diaphragm and comprises four side chamber walls and a back chamber wall.

7. The fabric acoustic sensor of claim 1, wherein the chamber wall comprises rigid foam.

8. The fabric acoustic sensor of claim 1, wherein the chamber wall secures the diaphragm such that the diaphragm is taut.

9. The fabric acoustic sensor of claim 1, further comprising one or more additional diaphragms.

10. The fabric acoustic sensor of claim 9, wherein the diaphragm and the one or more additional diaphragms are arranged in a grid and are regularly-placed.

* * * * *